United States Patent [19]

Morris et al.

[11] Patent Number: 5,037,854

[45] Date of Patent: Aug. 6, 1991

[54] SUBSTITUTED PHENONE

[75] Inventors: Howard R. Morris, London; Robert R. Kay, Cambridge; Mark S. Masento, Poole; Graham W. Taylor, London, all of United Kingdom

[73] Assignee: 3i Research Exploitation Limited, London, United Kingdom

[21] Appl. No.: 438,437

[22] PCT Filed: May 23, 1988

[86] PCT No.: PCT/GB88/00406

§ 371 Date: Jan. 22, 1990

§ 102(e) Date: Jan. 22, 1990

[87] PCT Pub. No.: WO88/09321

PCT Pub. Date: Dec. 1, 1988

[30] Foreign Application Priority Data

May 21, 1987 [GB] United Kingdom ............. 8712200

[51] Int. Cl.$^5$ ............................. A61K 31/12
[52] U.S. Cl. ........................ 514/687; 568/322; 568/319; 568/337
[58] Field of Search .............. 568/337, 319, 322; 514/687

[56] References Cited

U.S. PATENT DOCUMENTS

| 2,171,494 | 8/1935 | Kyridis ................ 568/337 |
| 2,929,848 | 3/1960 | Woodruff et al. ....... 568/337 |
| 3,335,164 | 8/1967 | Scherer et al. ........ 568/337 |
| 3,467,715 | 9/1969 | Broadbent et al. ...... 568/337 |
| 4,929,741 | 5/1990 | Fischli et al. ........ 568/337 |

FOREIGN PATENT DOCUMENTS

| 364883 | 12/1922 | Fed. Rep. of Germany ...... 568/319 |
| 317194 | 9/1929 | United Kingdom ............ 568/319 |

OTHER PUBLICATIONS

Mizobuchi et al., Chemical Abstracts, vol. 93, No. 7, Aug. 1980, Abstract 71294e.

Yao et al., Chemical Abstracts, vol. 103, 1985, Abstract 123103p.

Linde, Chemical Abstracts, vol. 100, 1984, Abstract 20465s and Arch. Pharm. (Weinheim) 1983, 316 (11), 971-972.

Chemical Abstracts, vol. 108, No. 15, Apr. 11, 1988, Abstract 128815k, "Structure Elucidation of Two Differentiation Inducing Factors (DIF-2 & DIF-3) From the Cellular Slime Mold *dictyostelium Discoideum*".

Nature, vol. 328, No. 6133, Aug. 27-Sep. 2, 1987, "Chemical Structure of the Morphogen Differentiation Inducing Factor From Dictyostelium *discoideum*", pp. 811-814.

Nature, vol. 303, No. 5914, pp. 242-244, 1983: R. R. Kay & K. A. Jermyn, "A Possible Morphogen Controlling Differentiation in Dictyostelium".

*Primary Examiner*—James H. Reamer
*Attorney, Agent, or Firm*—Scully, Scott, Murphy & Presser

[57] ABSTRACT

A compound which has the biological action of inducing cell differentiation has general chemical formula (I), in which $R_1$ is a straight or branched chain or cyclic alkyl or alkenyl group; $R_2$ is an alkoxy or hydroxy group; $R_3$ is a hydrogen or halogen atom; and, $R_4$ is a halogen atom. Preferred values for the groups are $R_1 = C_3$ to $C_8$ alkyl; $R_2 =$ methoxy; and, either or both of $R_3$ and $R_4 =$ chlorine. The compounds: 1) 2,6-dihydroxy-3,5-dichloro-4-methoxy valerophenone; 2) 2,6-dihydroxy-3,5-dichloro-4-methoxy butyrophenone; and, 3) 2,6-dihydroxy-3-chloro-4-methoxy valerophenone are of particular interest.

11 Claims, 2 Drawing Sheets

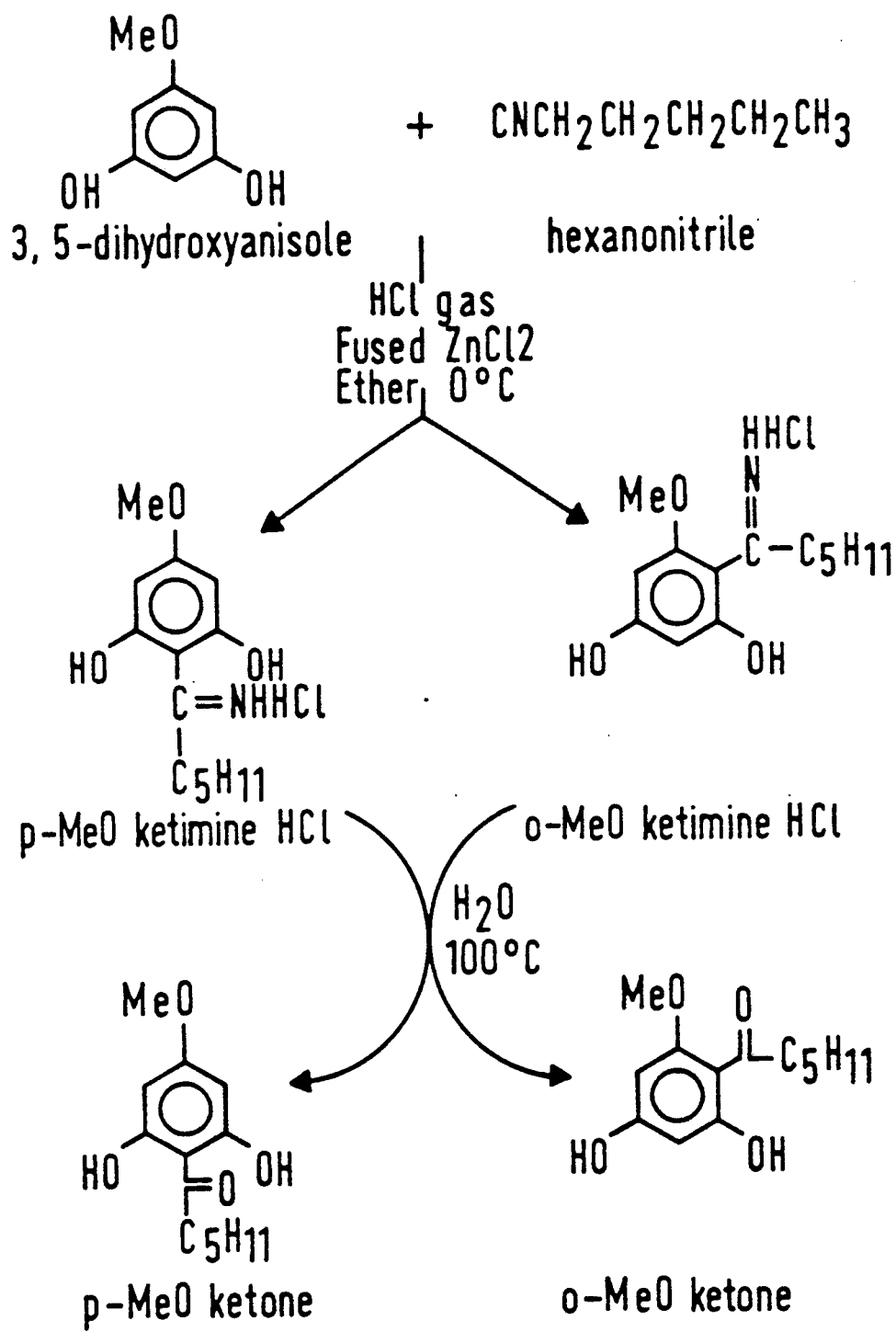
FIG. 1. Synthesis of the pentyl ketones of 3,5-dihydroxyanisole via the Hoesch reaction.

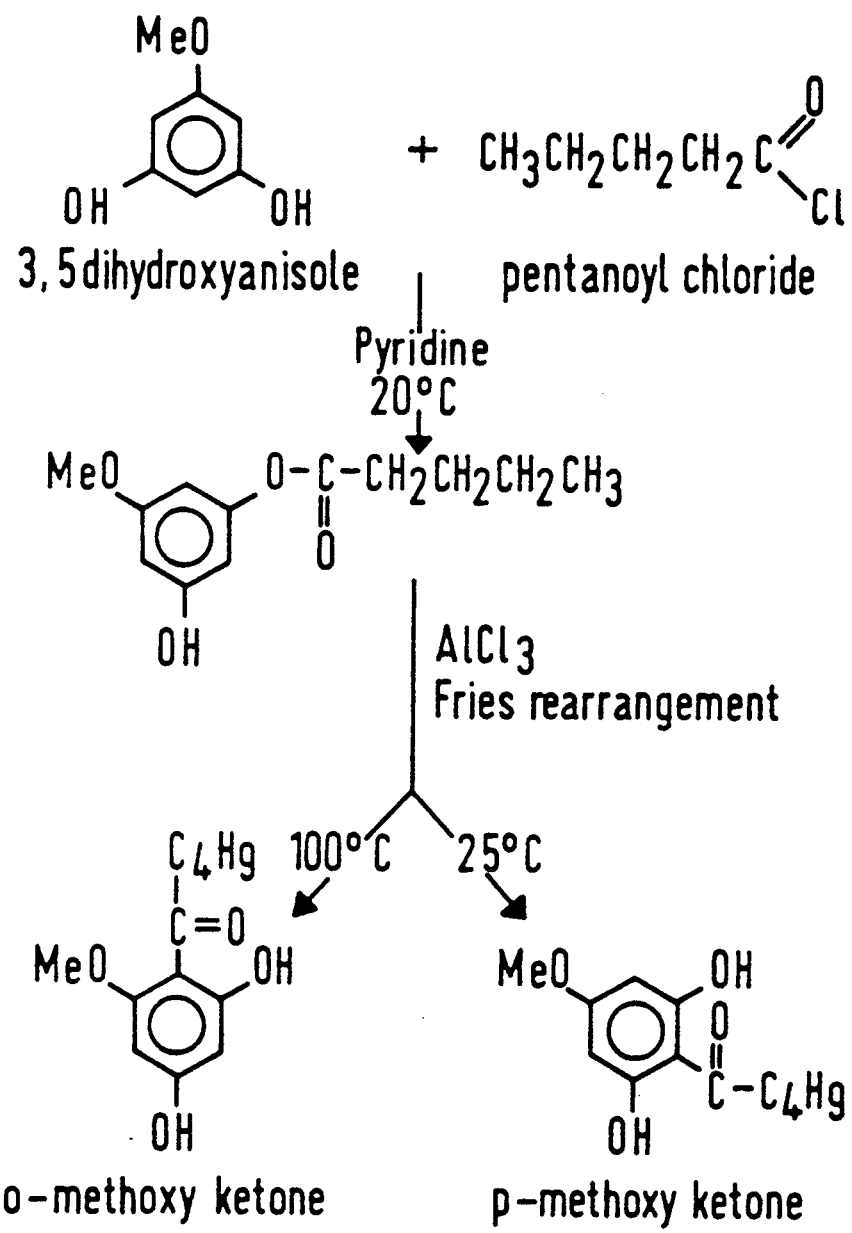
FIG. 2. Synthesis of the pentyl ketones of 3,5-dihydroxyanisole via the Fries reaction.

SUBSTITUTED PHENONE

This invention relates to a substituted phenone and to methods for the preparation thereof. More specifically, the invention relates to substituted phenones of which the substituents are selected from hydroxyl and methoxy groups and halogen atoms.

The present invention is concerned with a group of compounds which is related to a naturally occurring class of substances of hitherto unknown composition and structure. This is a group of biologically active substances which participates in the differentiation of cells, the degree of biological activity varying with the various substituent groups and isomers of the substituted phenone. The existence of one or more "differentiation inducing factors" (DIF) has been reported in the literature but the the composition and structure is unknown. Reference is made to the following which describe the discovery, isolation, purification and the biological role of DIF:

Nature, vol. 303, No. 5914, pp 242-244 (1983): R. R. Kay & K. A. Jermyn, "A possible morphogen controlling differentiation in Dictyostelium";

Eur. J. Biochem., 136, pp 51-56 (1983): R. R. Kay, B. Dhokia & K. A. Jermyn, "Purification of stalk-cell-inducing morphogens from Dictyostelium discoideum";

Nature, vol. 262, No. 5570, pp 717-719 (1976): C. D. Town, J. D. Gross & R. R. Kay, "Cell differentiation without morphogenesis in Dictyostelium discoideum"; and, Cell, vol. 33, 397-403 (1983): W. Kopachik, A. Oohata, B. Dhokia, J. J. Brookman and R. R. Kay, "Dictyostelium mutants lacking DIF, a putative morphogen".

The composition and structure of DIF has now been identified, by the inventors, as lying within the group of compounds which is the subject of the present invention.

According to the present invention there is provided a compound of the general formula I;

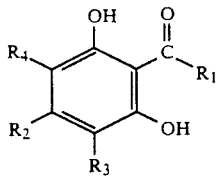

in which $R_1$ is a straight or branched chain alkyl or alkenyl group having from 3 to 8 carbon atoms;
$R_2$ is an alkoxy group;
$R_3$ is a hydrogen or halogen atom; and,
$R_4$ is a halogen atom.

The group $R_1$ has from 3 to 8 carbon atoms, examples of such being methyl, ethyl, n-propyl, iso-propyl, n-butyl, isobutyl, n-pentyl, isopentyl, hexyl, heptyl, octyl and octenyl.

Preferably, the group $R_2$ is a methoxy group, and either or both of $R_3$ and $R_4$ are halogen, most preferably chlorine, atoms.

The present invention also provides the compounds 2,6-dihydroxy-3,5-dichloro-4-methoxy valerophenone; 2,6-dihydroxy-3,5-dichloro-4-methoxy butyrophenone; and 2,6-dihydroxy-3-chloro-4-methoxy valerophenone. [The IUPAC nomenclature for these compounds is 1-[3,5-di-chloro-2,6-dihydroxy-4-methoxy)phenyl]-hexan-1-one; 1-[(3,5-dichloro-2,6-dihydroxy-4-methoxy)-phenyl]-pentan-1-one; and, 1-[(3-chloro-2,6-dihydroxy-4-methoxy)phenyl]-hexan-1-one, respectively.]

The present invention also provides a first method of preparing the above-defined compound of general formula I, comprising reacting together a compound of general formula II,

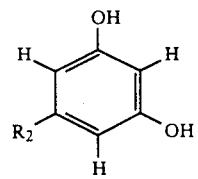

in which $R_2$ is as defined above with an alkanoyl chloride of formula $R_1.CO.Cl$ wherein $R_1$ is as defined above, to give a product having the general formula III;

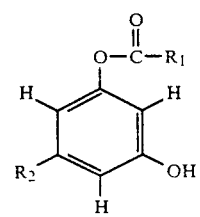

in which $R_1$ and $R_2$ are as defined above, and subjecting the compound of formula III to a Fries Rearrangement reaction in the presence of aluminium trichloride thereby to form a compound having the general formula IV;

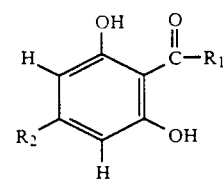

in which $R_1$ and $R_2$ are as defined above, followed by halogenation to give a compound having the general formula I defined above.

The reaction between the compound of formula II and the alkanoyl chloride is preferably carried out in pyridine solvent. The Fries Rearrangement may be effected at lower temperature (20°-30° C.) to favour formation of one isomer or at higher temperature (90°-100° C.) to favour formation of another isomer. For example, the reaction of 3,5-dihydroxy anisole with an alkanoyl chloride produces the compound defined by formula III above in which $R_2$ is methoxy and $R_1$ is an alkanoyl group. This may then be subjected to Fries Rearrangement at 25° C. to give the para-methoxy isomer or at 100° C. to favour the ortho-methoxy isomer (not included in this invention). The desired isomer can then be subjected to halogenation.

This reaction scheme is shown in FIG. 2 herewith, using 3,5-dihydroxyanisole and pentanoyl chloride for illustration. The halogenation step is exemplified in Example 2 below.

The invention also provides a second method of preparing the compound of general formula I defined above, comprising reacting an iminochloride of formula $R_1.C(=NH).Cl$ in which $R_1$ is as defined above, with a phenol having the general formula II;

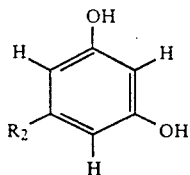
(II)

in which $R_2$ is as defined above, to form a ketimine hydrochloride having the formula V;

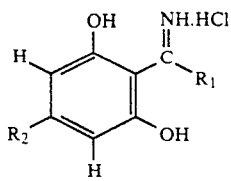
(V)

in which $R_1$ and $R_2$ are as defined above, and hydrolysing the said ketimine to form a compound of the general formula IV defined above, followed by halogenation to give a compound of the general formula I defined above.

In this process the iminochloride of formula $R_1.C(=NH).Cl$ is conveniently generated in situ by reaction of a nitrile of formula $R_1CN$ and HCl.

It is preferable, but not essential, that the reaction between the iminochloride and the phenol be carried out in the presence of anhydrous zinc chloride, ferric chloride or aluminium trichloride as a catalyst.

The second method is illustrated by the reaction scheme laid out in FIG. 1.

The invention will now be described, by way of illustration, by the following Examples.

EXAMPLE 1

One equivalent of 3,5-dihydroxyanisole was reacted with one equivalent of valeroyl chloride in pyridine as solvent for a period of one hour by the reaction scheme shown in FIG. 2. The solvent pyridine was removed from the reaction mixture to give 3-hydroxy-5-methoxyphenyl valerate (the monoester) and 5-methoxyphenyl-1,3-divalerate (the diester) in approximately equal amounts.

The isolated monoester intermediate (or in some experiments the crude mixture) was subjected to a Fries Rearrangement reaction in the presence of aluminium trichloride, as shown in FIG. 2, in dichloromethane (2 vols) by adding the ester over one hour and reacting at either 25° or 100° C. for four hours followed by standing overnight at room temperature.

The mixture of ketones was chlorinated as described in Example 2 below (where appropriate) and the product isolated by HPLC using C$_{18}$ Microbondapak (Trade Mark). The column was eluted isocratically in 65% of 5% acetic acid and 35% n-propanol.

EXAMPLE 2

Hexanenitrile was reacted with 3,5-dihydroxyanisole by the reaction scheme shown in FIG. 1 herewith for a period of 72 hours to produce the ketimine chloride shown. The ketimine chloride was dissolved in 20% (v/v) methanol in water. The products of hydrolysis were (1) an orange coloured oil (containing the ketone) which was retained on filtering and solidified on cooling, (2) a feathery off-white precipitate which developed as the filtrate cooled and (3) a yellow liquor.

The ketone, in chloroform, were halogenated (as appropriate) using a solution of the halogen in water at room temperature for five minutes with shaking. The process was repeated with fresh halogen water as appropriate to form the mono- or di-halo derivatives.

Using the methods described in Example 1 or Example 2, and appropriate starting materials, the compounds listed below have been prepared.

TABLE I

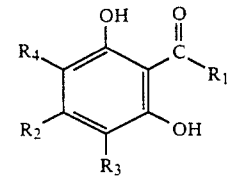

| No. | $R_1$ | $R_3$ | $R_2$ | $R_4$ |
|---|---|---|---|---|
| 1 | $C_3H_7$ | Cl | OMe | H |
| 2 | $C_3H_7$ | Cl | OMe | Cl |
| 3 | $C_4H_9$ | Cl | OMe | H |
| 4 | $C_4H_9$ | Cl | OMe | Cl |
| 5 | $i-C_4H_9$ | Cl | OMe | H |
| 6 | $i-C_4H_9$ | Cl | OMe | H |
| 7 | $C_5H_{11}$ | Cl | OMe | H |
| 8 | $C_5H_{11}$ | Cl | OMe | Cl |
| 9 | $C_5H_{11}$ | Br | OMe | H |
| 10 | $C_5H_{11}$ | Br | OMe | Br |
| 11 | $C_5H_{11}$ | I | OMe | H |
| 12 | $i-C_5H_{11}$ | Cl | OMe | H |
| 13 | $i-C_5H_{11}$ | Cl | OMe | Cl |
| 14 | $C_6H_{13}$ | Cl | OMe | H |
| 15 | $C_6H_{13}$ | Cl | OMe | Cl |
| 16 | $C_7H_{15}$ | Cl | OMe | H |
| 17 | $C_7H_{15}$ | Cl | OMe | Cl |
| 18 | $C_8H_{17}$ | Cl | OMe | H |
| 19 | $C_8H_{17}$ | Cl | OMe | Cl |

EXAMPLE 3

Test for Differentiation Inducing Activity

The compounds were tested for differentiation inducing activity by the procedure described in Euro. J. Biochem., 136, pp 51–56, (1983): R. R. Kay, B. Dhokia & K. A. Jermyn, "Purification of stalk-cell-inducing morphogens from *Dictyostelium discoidem*"

The following selection from Table I, given as Table II below, lists the most preferred compounds, being those which have been found to possess differentiation inducing activity.

TABLE II

| No. | $R_1$ | $R_3$ | $R_2$ | $R_4$ |
|---|---|---|---|---|
| 2 | $C_3H_7$ | Cl | OMe | Cl |
| 3 | $C_4H_9$ | Cl | OMe | H |
| 4 | $C_4H_9$ | Cl | OMe | Cl |
| 5 | $i-C_4H_9$ | Cl | OMe | H |
| 6 | $i-C_4H_9$ | Cl | OMe | Cl |
| 7 | $C_5H_{11}$ | Cl | OMe | H |
| 8 | $C_5H_{11}$ | Cl | OMe | Cl |
| 9 | $C_5H_{11}$ | Br | OMe | H |
| 10 | $C_5H_{11}$ | Br | OMe | Br |
| 12 | $i-C_5H_{11}$ | Cl | OMe | H |
| 13 | $i-C_5H_{11}$ | Cl | OMe | Cl |
| 14 | $C_6H_{13}$ | Cl | OMe | H |
| 15 | $C_6H_{13}$ | Cl | OMe | Cl |
| 17 | $C_7H_{15}$ | Cl | OMe | Cl |
| 19 | $C_8H_{15}$ | Cl | OMe | Cl |

EXAMPLE 4 (FOR COMPARISON)

In order to investigate the effects of altering the positions and identity of the various substituents in the phenyl ring, a very large number of isomers and analogues of the compounds found to be active were prepared. The activities of these related compounds were determined and compared with the most closely related cof the active compounds. The results are given in Table III below. The active compounds bear the reference number assigned in Table I above, the related but inactive compounds being referenced from number 100.

TABLE III

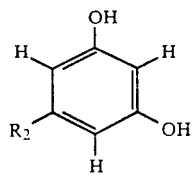

| No. | $R_1$ | A | $R_3$ | $R_2$ | $R_4$ | B |
|---|---|---|---|---|---|---|
| 2 | $C_3H_7$ | OH | Cl | OMe | Cl | OH |
| 100 | $C_3H_7$ | OMe | H | OH | H | OH |
| 101 | $C_3H_7$ | OH | H | OMe | H | OH |
| 102 | $C_3H_7$ | OMe | Cl | OH | Cl | OH |
| 8 | $C_5H_{11}$ | OH | Cl | OMe | Cl | OH |
| 103 | $C_5H_{11}$ | OMe | H | OH | H | OH |
| 104 | $C_5H_{11}$ | OMe | Cl | OH | H | OH |
| 105 | $C_5H_{11}$ | OMe | Cl | OH | Cl | OH |
| 106 | $C_5H_{11}$ | OH | H | OMe | H | OH |
| 17 | $C_7H_{15}$ | OH | Cl | OMe | Cl | OH |
| 107 | $C_7H_{15}$ | OMe | Cl | OH | Cl | OH |

These are but examples of the a large number of comparative tests which have been carried out and which demonstrate that cell differentiation activity is dependent upon there being an alkoxy group in the para-position to the ketone group, a halogen atom in either or both of the meta-positions with both ortho-positions occupied by hydroxyl groups.

A certain amount of biological evidence has been published that alkenyl chains may have activity in respect other than in cell differentiation and it is therefore indicated that value may be obtainable in inserting an alkenyl group as $R_1$. No alteration of the preparative procedure is required, merely selection of an appropriate starting material which contains an alkenyl rather than an alkyl group as exemplified hereinabove.

We claim:
1. A derivative of a phenone characterised in that it has the general chemical formula I:

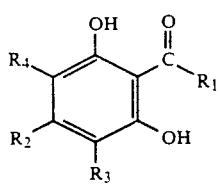

in which $R_1$ is a straight or branched chain alkyl or alkenyl group containing 3 to 8 carbon atoms;
$R_2$ is an alkoxy group;
$R_3$ is a hydrogen or halogen atom; and,
$R_4$ is a halogen atom.
2. A derivative as claimed in claim 1, characterised in that $R_2$ is a methoxy group.
3. A derivative as claimed in claim 1 or claim 2, characterised in that $R_3$ and $R_4$ are both halogen atoms.
4. A derivative as claimed in claim 3, characterised in that the halogen is chlorine or bromine or iodine.
5. The compound 2,6-dihydroxy-3,5-dichloro-4-methoxy valerophenone.
6. The compound 2,6-dihydroxy-3,5-dichloro-4-methoxy butyrophenone.
7. The compound 2,6-dihydroxy-3-chloro-4-methoxy valerophenone.
8. A method of preparing a derivative of a phenone characterised in that it comprises reacting together a compound of general formula II,

in which $R_2$ is as defined in claim 1 with an alkanoyl chloride of formula;

$R_1.CC.Cl$ wherein $R_1$ is as defined in claim 1, to give a product having the general formula III;

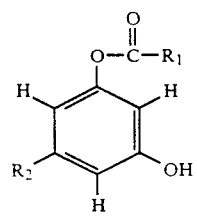

in which $R_1$ and $R_2$ are as defined in claim 1, and subjecting the compound of formula III to a Fries Rearrangement reaction in the presence of aluminium trichloride thereby to form a compound having the general formula IV;

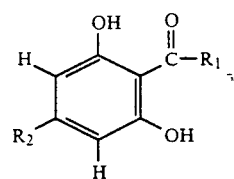

in which $R_1$ and $R_2$ are as defined in claim 1, followed by halogenation to give a compound having the general formula I defined in claim 1.
9. A method as claimed in claim 8, characterised in that the reaction between the compound of formula II and the alkanoyl chloride is carried out in pyridine solvent.
10. A method as claimed in claim 9, characterised in that the Fries Rearrangement is carried out at a temperature of around 25° C.
11. A biologically active preparation characterized in that it contains, as active principle, an amount of a compound having the general formula I claimed in claim 1 effective to provide cell differentiation activity.

* * * * *